US00PP31209P2

(12) United States Plant Patent
Korlipara

(10) Patent No.: US PP31,209 P2
(45) Date of Patent: Dec. 10, 2019

(54) ***GEUM* PLANT NAMED 'TNGEUTR'**

(50) Latin Name: ***Geum* hybrid**
Varietal Denomination: TNGEUTR

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/501,429

(22) Filed: Apr. 12, 2019

(51) Int. Cl.
*A01H 5/02* (2018.01)
*A01H 6/74* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct *Geum* plant named 'TNGEUTR' characterized by medium large, semi-double flowers that are rose-red and fade to light pink, mounding habit, heavy spring bloom with repeat bloom throughout the summer, and excellent vigor.

1 Drawing Sheet

Botanical designation: *Geum* hybrid.
Variety denomination: 'TNGEUTR'.

BACKGROUND OF THE INVENTION

The present invention relates to a new and distinct cultivar of *Geum* plant given the name 'TNGEUTR'. *Geum* is in the family Rosaceae. The new cultivar was bred using unknown, unnamed proprietary plants. The new cultivar was selected for its superior habit and flowering.

Compared to *Geum* 'Cosmopolitan' (U.S. Plant Pat. No. 24,982) the new cultivar has more rose-red flower color, with more and shorter flowering stems. In addition, the new cultivar reblooms sporadically summer through fall rather than only spring blooming.

Compared to *Geum* 'Mai Tai' (U.S. Plant Pat. No. 22,433) the new cultivar is has more rose-red flower color rather than orange. In addition the new cultivar reblooms sporadically summer through fall rather than only spring blooming.

Compared to *Geum* 'Cherry Bomb' an unpatented cultivar, the new cultivar has a higher flower count and reblooms sporadically summer through fall rather than only spring blooming.

SUMMARY OF THE INVENTION

The following traits have been repeatedly observed and are determined to be the unique characteristics of 'TNGEUTR'. These characteristics in combination distinguish 'TNGEUTR' as a new and distinct cultivar:

1. medium large flowers that are rose-red and fade to light pink,
2. semi-double flowers,
3. good flower size,
4. heavy blooming,
5. dense, deep green foliage with attractive leaves,
6. a compact, mounding habit,
7. heavy spring bloom with repeat bloom throughout the summer and fall, and
8. excellent vigor.

This new cultivar has been reproduced only by asexual propagation (cuttings and tissue culture using apical bud). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

The Trademark designation of the new cultivar is TEMPO™ Rose.

BRIEF DESCRIPTION OF THE DRAWINGS

FIG. 1 shows a photo of a nine-month-old *Geum* 'TNGEUTR' reblooming in the trial field in November in Canby, Oreg.

FIG. 2 shows a one-year-old *Geum* 'TNGEUTR' growing in the trial field in April in Canby, Oreg.

DETAILED PLANT DESCRIPTION

The following is a detailed description of the new *Geum* cultivar based on observations of two-year-old specimens growing in a trial field in full sun under typical outdoor conditions in late May in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 2007, 5$^{th}$ edition.

Plant:

*Type*.—Herbaceous perennial.

*Hardiness*.—USDA Zone 5-9.

*Size*.—39 cm wide and 26 cm tall to top of the foliage, 64 cm to top of flowers.

*Form*.—Mound with 30 to 50 crowns.

*Persistence*.—Dies down to the crown in winter.

*Vigor*.—Excellent.

*Stem*.—None.

Leaf:

*Type*.—Simple, rosulate.

*Arrangement*.—Basal rosette.

*Surface texture*.—Pubescent on both sides.

*Venation*.—Pinnate and impressed.

*Number*.—250.

*Petiole*.—Grows to 13.2 cm long and 0.5 mm wide (0.8 mm wide at base), pubescent, closest to Yellow Green 146 C, petiole base clasping.

*Rosulate leaves*.—Lyrate-pinnate, 7-foliate, with leaflets in pairs in declining size below the terminal leaflet (smallest to 0.3 mm wide, 0.3 mm long); terminal leaflet largest, rhomboid, grows to 8.7 cm long and 9.2 cm wide, 3-5 lobed, truncate base, margins irregularly serrate, tip obtuse to notched to acute; top lateral leaflets, 3.9 cm wide, 3 cm long, irregularly obovate, margins irregularly serrate, opposite, tips acute to obtuse, bases cuneate, sessile.

*Color*.—Topside Green 137A including veins, bottom side Green 138B with veins Green 138B.

Inflorescence:

*Description*.—In cymes, 2 to 4 cymes from each crown with 4 to 7 flowers per cyme.

*Flowering stem attitude*.—Upright to semi-upright.

*Peduncle*.—Grows to 38 cm tall and 3.5 mm wide, pubescent, Yellow Green 144B where shaded and Greyed Purple 187A where exposed to sun.

*Peduncle leaves*.—Lyrate, petiolate with petioles to 8 mm long, blade grows to 2.6 cm long and 2 cm wide, 3-lobed, serrate, tips attenuate, base cuneate, pubescent on both sides; stipules large adnate to petiole, foliar, grow to 1 cm long and 1.5 cm wide, irregularly incised, pubescent on both sides; leaves and stipules topside Green 137A including veins, bottom side Green 138B with veins Green 138B.

*Peduncle strength*.—Very strong.

*Rachis*.—Grows to 10 cm wide and 24 cm long pubescent, Greyed Purple 187A.

*Pedicel*.—Variable in length, 4.5 cm to 10.5 cm long and 2 mm wide, Greyed Purple 187A.

Flower bud:

*Size*.—1 cm long and 1 cm wide.

*Shape*.—Conic, nodding.

*Surface*.—Pubescent.

*Color*.—Greyed Purple 187C.

Flower:

*Type*.—Actinomorphic, semi-double.

*Size*.—3.3 cm wide and 1 cm deep.

*Flower attitude*.—Side-facing.

*Flower number*.—420.

*Corolla description*.—Usually 8-11 petals, broadly obovate in shape, grows to 1.1 cm deep and 1.4 cm wide, tip notched to sometimes obtuse, base truncate, glabrous on both sides, young petals Yellow White 158A tinted with Greyed Purple 184C, bottom side Yellow White 158A; older flowers top side fade into Greyed Purple 184C, bottom side Greyed Purple 184D tinted with Yellow White 158A.

*Calyx description*.—5 main sepal lobes alternating with 5 smaller lobes, stellate, 28 mm wide overall, Greyed Purple 185C inside, outside Greyed Purple 187A, pubescent outside and glabrous inside, lobes triangular, margins entire, tips acuminate and reflexed, main lobes 7 mm long and 6 mm wide, smaller lobes 2.5 mm long and 0.5 mm wide.

*Pistil description*.—About 100 hair-like pistils forming a clump 2 cm in diameter, stigma 1 in number, style 11 mm long, 0.1 wide, ovary 2.5 mm long and 2 mm wide, Yellow Green 144A and covered with white hairs; Yellow Green 146C tinted Greyed Orange 175A near stigma.

*Stamen description*.—About 120, 5 mm long, filaments 4 mm long, Yellow Green 145C, anthers 1 mm long, Yellow 8A, pollen Yellow 13B.

*Fragrance*.—None.

*Lastingness*.—Each flower last approximately one week in summer and up to two weeks in cool weather.

*Bloom time*.—April to May with rebloom through November.

Fruit:

*Type*.—A head of achenes, single beaked.

*Number*.—Over 60 per bloom on average.

*Size*.—1 cm long, 2 mm wide.

*Color*.—Green 143C at base for 2 mm, blending to Greyed Orange 166A for 8 mm.

*Texture*.—Pubescent.

Seed:

*Shape*.—Tear shaped.

*Size*.—2.5 mm long, 2 mm wide.

*Color*.—Brown 200A.

*Texture*.—Smooth.

Disease and pests: The new cultivar is typical to the genus. No known resistances to pests or diseases.

I claim:

1. A new and distinct *Geum* plant as herein illustrated and described.

* * * * *

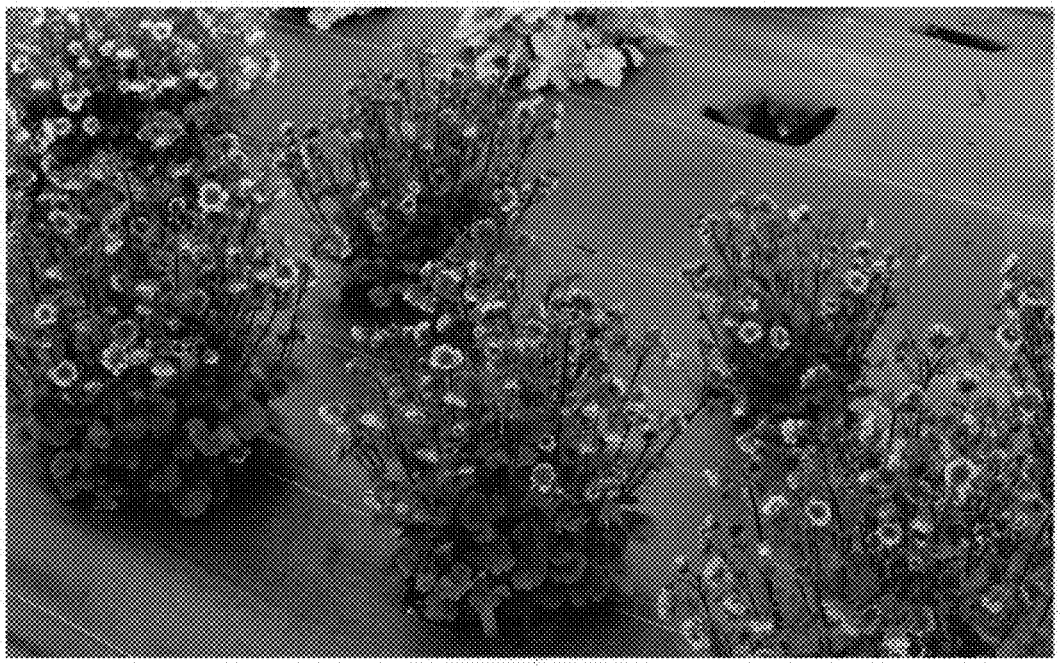

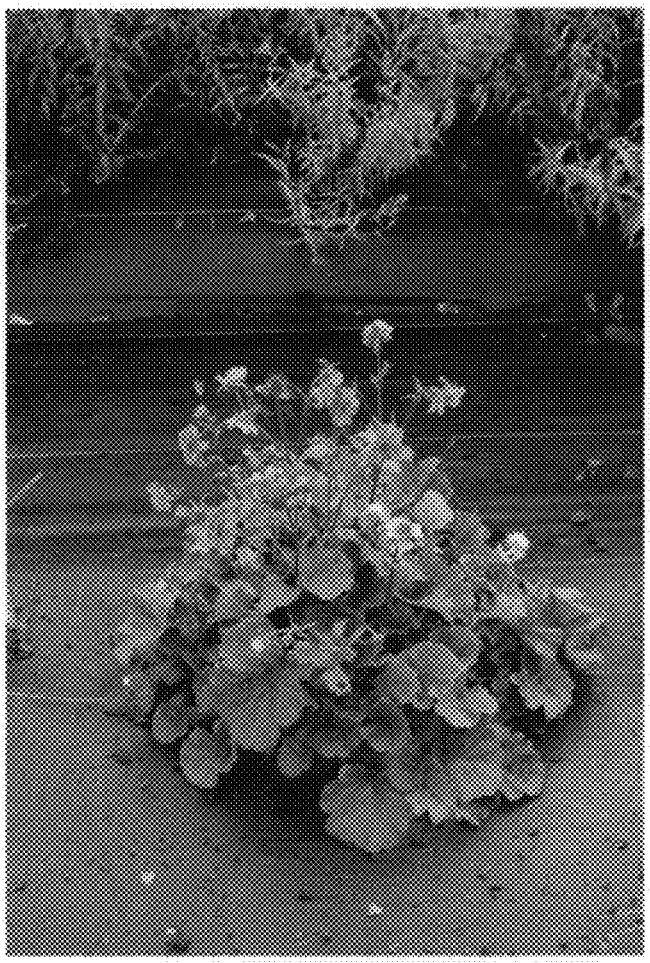
Fig. 1 Left
Fig. 2 Below